(12) United States Patent
Kawai et al.

(10) Patent No.: US 8,992,998 B2
(45) Date of Patent: Mar. 31, 2015

(54) MAPK INHIBITION BY $H_2$

(76) Inventors: Toshihisa Kawai, Brookline, MA (US);
Mikihito Kajiya, Brookline, MA (US);
Kimihiro Sato, New York, NY (US)

( * ) Notice: Subject to any disclaimer, the term of this patent is extended or adjusted under 35 U.S.C. 154(b) by 0 days.

(21) Appl. No.: 13/820,209

(22) PCT Filed: Sep. 2, 2011

(86) PCT No.: PCT/US2011/050310
§ 371 (c)(1),
(2), (4) Date: Jun. 24, 2013

(87) PCT Pub. No.: WO2012/031189
PCT Pub. Date: Mar. 8, 2012

(65) Prior Publication Data
US 2013/0266540 A1 Oct. 10, 2013

Related U.S. Application Data

(60) Provisional application No. 61/379,568, filed on Sep. 2, 2010.

(51) Int. Cl.
*A01N 59/00* (2006.01)
*A23L 2/52* (2006.01)
*A61K 33/00* (2006.01)
*C25B 1/04* (2006.01)

(52) U.S. Cl.
CPC . *A61K 33/00* (2013.01); *A23L 2/52* (2013.01); *C25B 1/04* (2013.01); *Y02E 60/366* (2013.01)
USPC ...................................... 424/600; 204/157.52

(58) Field of Classification Search
USPC ...................................... 424/600; 204/157.52
See application file for complete search history.

(56) References Cited

U.S. PATENT DOCUMENTS

2002/0009730 A1* 1/2002 Chenchik et al. ................. 435/6
2007/0261950 A1* 11/2007 Sato et al. ................ 204/157.52

OTHER PUBLICATIONS

Cardinal J. et al. Oral Hydrogen Water Prevents Chronic Allograft Nephropathy in Rats. Kidney International. online Nov. 11, 2009, pp. 1-9.*
Dixon B. et al. The Evolution of Molecular Hydrogen. Medical Gas Research 3(10)1-12, 2013.*
Liu G. et al. Molecular Hydrogen Regulates the Expression of miR-9 . . . Int J Ophthalmol 6(3)1-6, Jun. 2013.*
Xie K. et al. Hydrogen Gas Improves Survival Rate and Organ Damage in Zymogen Induced Generalized Inflammation Model. Shock 34(5)495-501, Nov. 2010.*
Cruse, J et al. Illustrated Dictionary of Immunology. Taylor & Francis, CRC Press 2003, pp. 335-336.*
Cornell T. et al. Mitogen Activated Protein Kinase Phosphatase 2 Regulates the Inflammatory Response in Sepsis. Infection and Immunity 78(6)2868-76, Mar. 29, 2010.*

* cited by examiner

*Primary Examiner* — Ralph Gitomer
(74) *Attorney, Agent, or Firm* — Kohn & Associates PLLC

(57) ABSTRACT

A method of treating inflammation in a subject by administering a composition including hydrogen, releasing hydrogen in the subject, suppressing mitogen-activated protein kinase (MAPK) phosphorylation and upregulating expression of MKP-1, and down-regulating inflammatory responses of monocyte lineage cells.

9 Claims, 10 Drawing Sheets

Figure 8
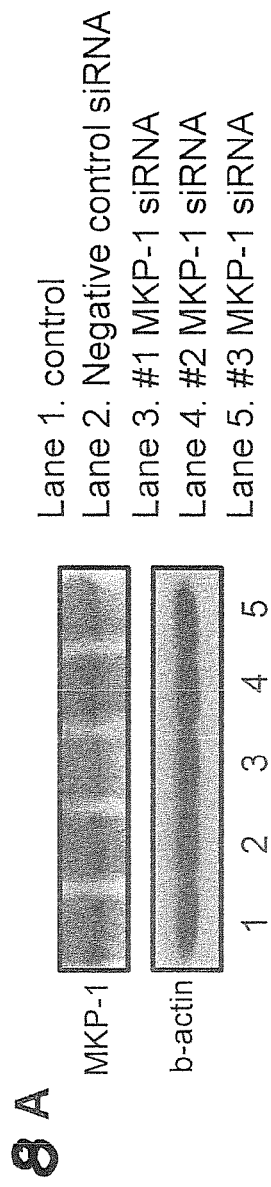
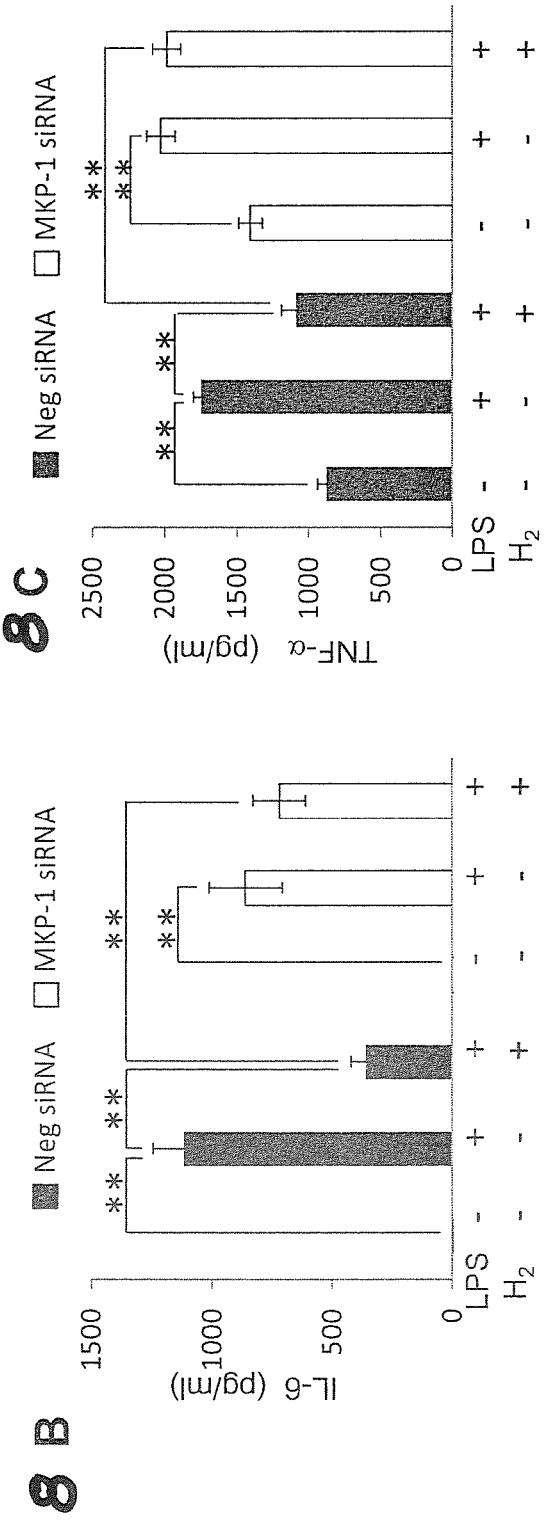

MAPK INHIBITION BY $H_2$

This application is a National Stage application filed under Rule 371 based upon PCT/US11/50310 filed Sep. 2, 2011, which claims benefit to provisional application 61/379,568 filed Sep. 2, 2010.

BACKGROUND OF THE INVENTION

1. Technical Field

The present invention relates to the effects of the administration of hydrogen and the increase of hydrogen in the body with regard to health promoting benefits. In particular, the present invention relates to effects of an aqueous solution including hydrogen suppressing the biological cell-signaling mechanism that causes inflammation.

2. Background Art

It has previously been reported that molecular hydrogen ($H_2$) dissolved in water, due to its antioxidant effects, has therapeutic value in the mouse model of brain injury induced by ischemia reperfusion. More specifically, the ability of $H_2$ to reduce the reactive oxygen species (ROS) generated in the course of brain injury was revealed to be responsible for this $H_2$-mediated therapeutic effect. Following this study, several other reports demonstrated that $H_2$ could suppress tissue injury in organs, such as liver, intestine, kidney and heart, caused by oxidative stress following ischemia reperfusion or transplantation induced graft injury. In addition, recently, Applicants revealed that $H_2$ can also exert anti-inflammatory effects by demonstrating the $H_2$-mediated protective effects in DSS-induced colitis model and cocanavalin A-induced hepatitis. However, since the biological processes of inflammation and oxidative stress are closely associated, the precise mechanism whereby $H_2$ prevents inflammatory response has remained unclear.

Mitogen-activated protein kinase (MAPK) signal transduction pathways play a key role in inflammatory cell signaling. MAPK pathways can be activated by a wide variety of inflammatory stimuli including one mediated by bacterial endotoxin, lipopolysaccharide (LPS), and different stress acting through diverse receptor families, including hormone receptors, growth factor receptors or cytokine receptors, seven-transmembrane receptors and through environmental stresses such as osmotic shock, ionizing radiation and ischemic injury. MAPK pathways, in turn, coordinate activation of gene transcription, protein synthesis, cell cycle machinery, cell death, and differentiation, in the context of inflammatory and stress responses.

Mammalian MAP kinases can be divided into three groups based on their structure and function: extracellular signal-regulated kinase (ERK), c-Jun N-terminal kinase or stress activated protein kinase (JNK or SAPK), ERK5 or BMK, and p38 group. A variety of extracellular stimuli produce cellular responses via activation of the MAP kinase cascades. To date three MAP kinase pathways, ERK, JNK, and p38, have been reported to be activated by LPS stimulation in macrophages.

ERK is the first group of MAP kinases that was found to be activated by LPS stimulation. In response to LPS stimulation, two tyrosine phosphorylated MAP kinase proteins, p42 (ERK2) and p44 (ERK1), can be detected in macrophages. Activation of ERKs can occur via the upstream effector, Ras. Upon stimulation, Ras interacts with the NH2-terminal domain of Raf-1, leading to its recruitment to the plasma-membrane, whereupon Raf-1 is phosphorylated by another kinase. Once activated, Raf-1 can phosphorylate MAP kinase kinase-1 (MKK-1, also known as MEK), which in turn, phosphorylates ERK.

Upon exposure to LPS, ERK-½ and its upstream activator, MEK-1 has been shown to be activated in monocytes, which elicits production of TNF-α or IL-1b in response to LPS treatment, indicating that ERKs may be involved in the signaling pathway that results in cytokine synthesis following LPS treatment. The Ras and Raf-1 components of the ERK cascade have been suggested to be necessary for LPS-stimulated TNF-α production. This was shown from the ability of LPS to induce rapid phosphorylation of Raf-1 in macrophages, activating the MEK-1/ERK pathway. However, while up-regulation of Raf-1 has been shown to strongly activate ERK1 and ERK2, it causes only a small increase in TNF-α mRNA expression, and protein secretion. Thus, the ERK pathway only partially mimics LPS effects, implying that other signaling pathways triggered by LPS may also play a role. Indeed, it has been demonstrated that LPS stimulation leads to the activation of multiple signal pathways, including JNK, and p38 MAP kinase pathways.

Both JNK1 and JNK2 have been reported to be activated in LPS treated macrophages. As their name indicates, the JNK proteins are associated with the phosphorylation of c-Jun. In addition, other transcription factors, including activating transcription factor-2 (ATF-2), and ternary complex factor (TCF) have been reported to be downstream targets for JNK. c-Jun can complex with c-fos or ATF2 which constitutes AP-1 or CRE binding activity. TCF mediated c-fos expression also influences c-Jun/c-fos dimer formation which would have impact on AP-1 binding activity. Since AP-1 and CRE sites are found in many cytokine promoters including TNF-a, regulation of AP-1 and/or CRE binding activity by JNK pathway plays important role in LPS induced cytokine expression. In addition, c-Jun complexes have been shown to act synergistically with NF-k B in LPS-treated monocytes to enhance the induction of TNF-α.

p38 (or p38a, also known as CSBP and RK) was initially isolated and cloned through a study designed to identify proteins in macrophages and pre-B cells that tyrosine phosphorylated in response to LPS. p38a was also cloned as a specific target of pyridinyl imidazole derivatives such as SB203580 which inhibit the production of proinflammatory cytokines by monocytes. Four isoforms of the p38 MAP kinases have been cloned and characterized: p38 (p38a), p38b, p38gamma (also known as ERK6 or SAPK3), and p38delta (also known as SAPK4), each of which contains a TGY dual phosphorylation motif between domains VII and VIII—distinguishing them from the ERK kinases (TEY) and JNK kinases (TPY). p38a and p38b are sensitive to SB203580 inhibition, but the activity of p38gamma and p38delta are unaffected. The discovery of a specific inhibitor of p38 SB203580 has provided a useful tool for dissecting the role of p38 kinases in septic shock, while its application to human patients has not been approved by FDA. Studies have demonstrated that inhibition of p38 in monocytes prevents LPS-stimulated production of IL-1b and TNF. It is clear that p38 pathways play a crucial role in LPS induced cytokine expression. However, the precise mechanism by which p38 regulates cytokine gene expression is still uncertain.

The MAPK signal transduction pathway also plays a central role in regulating tumor cell growth, survival, differentiation, and angiogenesis. The key components of the MAPK signal module (Ras/Raf/MEK/ERK) are frequently altered in human cancers. Targeting this pathway represents a promising anticancer strategy. Mutations in the small molecular weight G-proteins "Ras family" of proto-oncogenes are very common, being found in 20% to 30% of all human tumors. Therefore, Raf-MEK-ERK MAPK pathway represents one of the best characterized Ras signaling pathways which play a key role in growth of certain types of cancer cells. Raf and MEK have consequently emerged as key protein kinases to target for anticancer drug design. As noted above, while there exist multiple MAP kinase families, e.g. c-Jun N-terminal kinase (JNK) and p38, which are also activated downstream of small molecular weight G-proteins, ERK has been the best characterized and is more pertinent to aberrant signaling in human cancer. For some cancers, especially those of hematopoietic origin, the p38 and JNK pathways may in fact yield targets exploitable for anticancer drug development. However, a broad array of solid tumors is known to express constitutive levels of phosphorylated ERK1 and ERK2. Activation of ERK is critical for a large number of Ras-induced cancer cell responses.

MAP kinase phosphatases (MKPs) are a class of molecule that suppresses MAP kinase activity. MKPs are dual-specificity phosphatases (DUSPs) that recognize the TXY (Threonine: X-amino acid: Tyrosine) amino acid motif present in MAPK family members. More specifically, MKPs are uniquely able to hydrolyze the phosphate ester bond on both a tyrosine (Y) and a threonine (T) residue on the same protein. MKP expression can be induced by factors that activate MAPKs, such as environmental stresses and growth factor stimulation. Among a total of 11 MKP family members, the most frequently studied member of the MKP family is MKP-1. MKP-1 can dephosphorylate all three members of the MAPK family, but it has a much higher affinity for JNK and p38, with a much lower affinity for ERK. Given the pivotal role of MKP-1 in innate immunity, there is growing interest in exploring how its gene expression and biochemical activity are regulated. Expression of MKP-1 is induced by a number of growth factors and stresses in multiple cell types. In macrophages responding to activation of TLR by its ligand, such as LPS, there is a strong and rapid induction of MKP-1 mRNA and increase in MKP-1 protein abundance, peaking at 1 hour after stimulation. The induction of MKP-1 correlates with a decline in the activities of JNK and p38 MAPK, which is consistent with a role for MKP-1 in the inactivation of these MAPKs as a feedback mechanism to restrain excessive inflammation.

Therefore, there is a need for a composition that can modulate the level of MAPK at the cellular level in order to reduce and control inflammation.

SUMMARY OF THE INVENTION

The present invention also provides for a method of treating and protecting a subject from endotoxin shock, by administering a composition including hydrogen, releasing hydrogen in the subject, and down-regulating production of TNF-α and IL-6.

The present invention provides for a method of treating inflammation in a subject, by administering a composition including hydrogen, releasing hydrogen in the subject, and down-regulating inflammatory responses of monocyte lineage cells.

The present invention provides for a method of suppressing hydroxyl radical in a subject by administering a composition including hydrogen, releasing hydrogen in the subject, and suppressing hydroxyl radical.

The present invention provides for a method of treating inflammation in a subject, by administering a composition including hydrogen, releasing hydrogen in the subject, suppressing mitogen-activated protein kinase (MAPK) phosphorylation, and down-regulating inflammatory responses.

The present invention provides for a method of reducing the basal level of phosphorylation of MAPKs in non-stimulated monocyte lineage cells in a subject, by administering a composition including hydrogen, releasing hydrogen in the subject, and reducing basal levels of phosphorylation of MAPKs of extracellular signal-regulated kinase (ERK), p38, and c-Jun N-terminal kinase (JNK) in non-stimulated BMMs.

The present invention also provides for a method of performing a drug screen test to test for compounds that can treat endotoxin shock, by performing an assay for measuring the production of biomarkers IL-6 and TNF-α by applying drug candidates to the assay, and if drug candidates down-regulate IL-6 and TNF-α, identifying the drug candidates as being successful in treating endotoxin shock.

The present invention provides for a method of performing a drug screen test to test for compounds that can suppress hydroxyl radical, by performing an assay for measuring the production of biomarkers hydroxyl radical by applying drug candidates to the assay, and if drug candidates suppress hydroxyl radical, identifying the drug candidates as being successful in treating hydroxyl radical.

The present invention provides for a method of performing a drug screen test to test for compounds that can treat inflammation by performing an assay for measuring the production of biomarker MPK-1 by applying drug candidates to the assay, and if drug candidates up-regulate MPK-1, identifying the drug candidates as being successful in treating inflammation related to the MAPK phosphorylation pathway.

The present invention further provides for a diagnostic method for diagnosing patients with diseases caused by the MAPK pathway, by measuring biomarkers chosen from the group consisting of IL-6, TNF-α, IL-12p40, hydroxyl radical, MKP-1, or combinations thereof in a patient sample, comparing the measurements with a control value, and if the measurements are up-regulated or down-regulated, diagnosing the MAPK pathway as causing disease in the patient.

DESCRIPTION OF THE DRAWINGS

Other advantages of the present invention are readily appreciated as the same becomes better understood by reference to the following detailed description when considered in connection with the accompanying drawings wherein:

FIG. 8A is an immunoblot, and FIGS. 8B-8C are graphs of IL-6 and TNF-α production;

DETAILED DESCRIPTION OF THE INVENTION

Figure 1:
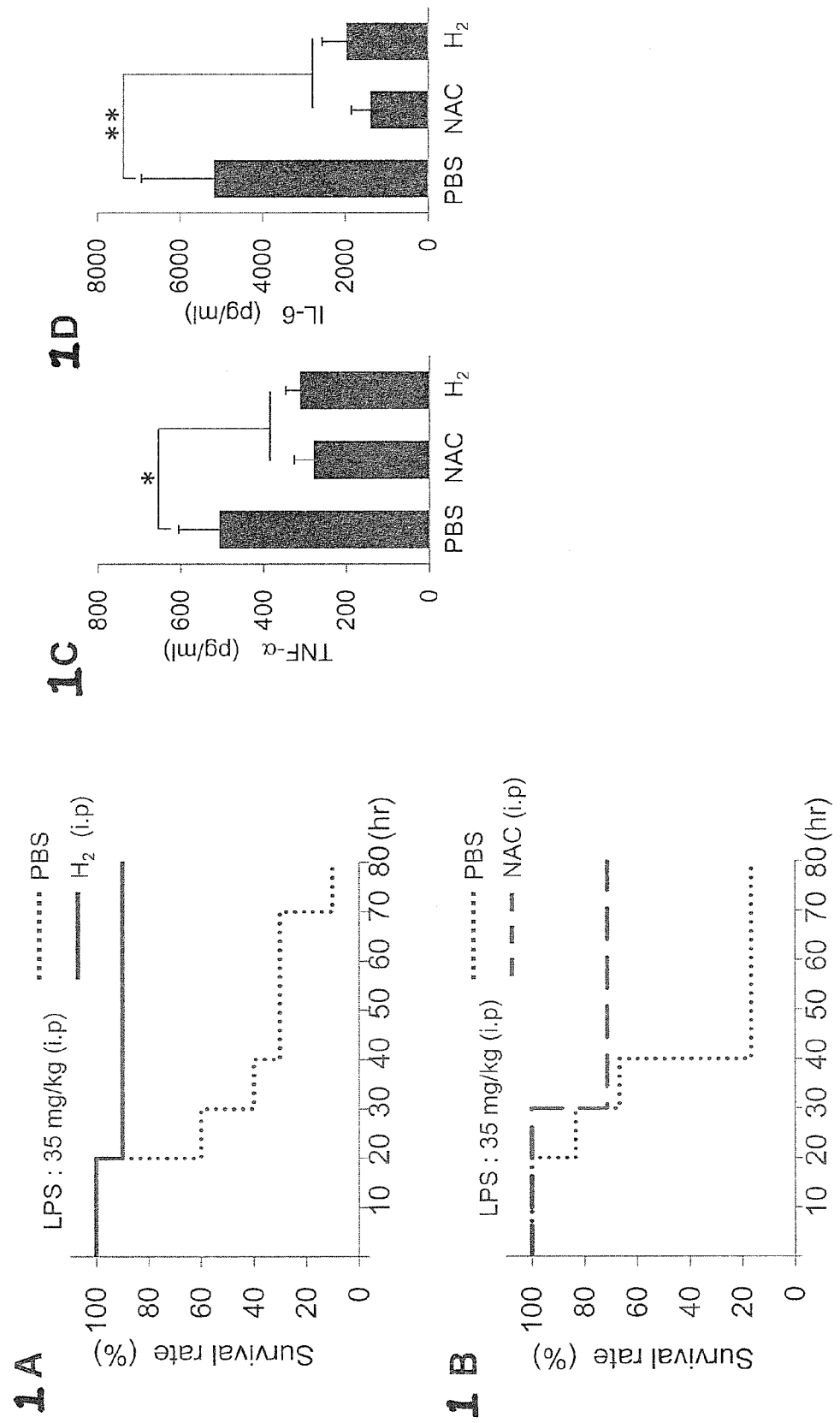
FIGS. 1A and 1B are graphs of LPS challenge.
FIGS. 1C and 1D are graphs of production of TNF-α and IL-6, respectively.

The present invention most generally is related to compositions including hydrogen used for suppressing and/or reducing inflammation. More specifically, the compositions are useful for suppressing the phosphorylation of mitogen-activated protein (MAP) kinases, a group of cell signaling molecules that respond to extracellular inflammatory stimuli (mitogens, osmotic stress, heat shock and proinflammatory cytokines) and regulate various inflammatory cellular activities, such as gene expression, mitosis, differentiation, proliferation, and cell survival/apoptosis. The hydrogen introduced into a body or applied to the body surface also suppresses the inflammation elicited by stimulation with bacterial components, such as endotoxin shock.

"Hydrogen" as used herein, refers to the composition $H_2$ (also written herein as H2), but can also include molecular hydrogen (H) and any composition capable of releasing hydrogen. In other words, H2 per se can be administered or a prodrug able to release H2 can be administered. Alternatively, any mimic drug can be used. Hydrogen can be administered by various means as described below, but preferably as an aqueous solution.

"Water" as used herein, refers to the composition $H_2O$ and is preferably enriched with hydrogen. The water can include ions and can be neutral or another pH.

"NIW" as used herein, refers to neutral ionized water, and is generally described in U.S. patent application Ser. No. 11/678,129 to Sato, et al., incorporated herein. Applicants previously discovered that hydrogen, preferably when dissolved in water, i.e. an aqueous solution, acts to suppress inflammation induced to cells in the body. NIW containing hydrogen can be administered as a drink, topical solution, or injection, among other methods of administration further described below. The NIW in Ser. No. 11/678,129 was shown to inhibit the production of proinflammatory cytokines including IL-1β and TNF-α and that hydrogen is the active component that that elicits an anti-inflammatory effect in cells. NIW is one example of water that can be used in the present invention.

Briefly, the NIW in the present invention can be prepared as follows. Electrolysis of water can be performed within a diaphragm or diaphragmless electrolytic cell that is equipped with multiple electrodes, an oscillating stirrer, a self-recirculating connecting tube or a remote agitator can be used. The remote agitator equipped to the Buffer Puffer™ self-recirculating electrophoresis bath offers the generation of sufficiently efficient recirculation of water during the electrolysis process to prevent the formation of pH or ion gradients. Using Buffer Puffer A5 system, the electrolysis of 0.1% NaCl solution (constant 30 mA currency, room temperature) for more than two hours results in the increase of pH from 6.94 to 11.16. However, as the water is agitated by a magnetic stirrer during the electrolysis of 0.1% NaCl solution (constant 30 mA currency, room temperature), the pH of the water remains stable (0 hour, pH 6.94; 8 hour, pH 7.01). Preferably, the agitator is a magnetic stirrer. The remote magnetic stirrer can be any magnetic stirring device known to those of skill in the art. The stirrer can be placed not within, but underneath, the machine. The benefit of such placement is that the stirrer is still able to stir the water without contaminating the water. For example, a white Teflon®, a homopolymer of tetrafluoroethylene sold by DuPont, coated stirring bar, is placed in position underneath the machine. This configuration eliminates possible contamination of the water. The neutral ionized water is produced by dissolving a small amount at least one kind of salt, e.g., $CaCl_2$, NaCl, Ca-lactate, or $NaHCO_3$ at concentration ranged between 0.05-0.2%, but is not limited to, in water, e.g., tap water, distilled water, soft water, de-ionized water and RO (reverse osmosis membrane) water. Especially, the salt that does not contain Cl (Chloride), such as Ca-lactate or $NaHCO_3$, can generate neutral ionized water without toxic derivative hypochlorite. Electrolysis is carried out by means of a direct current or pulsed current, while maintaining the voltage within a range of 1 to 30 V, and maintaining the current density within a range of 5 to 300 A/dm². The water is subjected to electrolysis at low water temperatures, at a range between 4-9 degrees C., but is not limited to this. Hydrogen can also be injected into the water for elongating the shelf life of the water.

"Neutraceutical" as used herein, refers to a food (or part of a food) that provides medical or health benefits, including the prevention and/or treatment of a disease. A neutraceutical can include dietary supplements and processed foods such as cereals, soups, and beverages.

The term "biomarker" as used herein refers to a substance, such as, but not limited to, a biological compound, protein, DNA sequence, RNA sequence, or other biological sequence that, when detected, indicates a particular disease state or propensity to develop a particular disease state. Biomarkers can be detected in a patient to diagnose disease or a health condition. Biomarkers can also be used to personalize therapeutic treatment.

The composition including hydrogen used in the methods described herein is most preferably the NIW and in neutraceutical form. However, any other composition can be used that includes hydrogen or is capable of generating hydrogen and increasing the concentration thereof in the body, and various administration procedures can be used as further described below. For example, water can be used that is directly dissolved with hydrogen gas. Such water can be prepared by bubbling hydrogen through water. High purity H2 gas can be ejected into water or any form of solutions until H2 concentration reached to saturation (780 mM, at 25° C.). The ejection of H2 into water at the 4 L/min for 1 minute reaches the saturation. The saturated H2 in water showed pH 7.6 and very high redox potential (ORP level −511 mV). H2 can be also released from a probiotic approach. The bacterium known to produce hydrogen, such as *Escherichia coli*, or bacterium that is genetically transformed to produce hydrogen, can be used as a H2 delivery vehicle. Any materials that can absorb and release H2, such as metal and alloys, can be used as an H2 delivery vehicle. Since H2 in atmosphere or H2 dissolved in solution can penetrate into body through skin or lung, respectively, an H2-chamber or H2-bath can be used to increase the H2 in the body.

Several methods are described herein that most generally relate to preventing and treating inflammation and its causes by the administration of the composition described above. The composition releases hydrogen into the patient's body, which then interacts with various cells and/or molecules to prevent and treat inflammation or various other conditions.

The present invention provides for a method of treating and protecting a subject from inflammation, exemplified by endotoxin shock, via administering a composition including hydrogen, releasing hydrogen in the body of the subject, and down-regulating production of TNF-α and IL-6. Preferably, the composition including hydrogen is the NIW, or H2-enriched water, or any of the other compositions described above. Endotoxin shock is caused by a systemic inflammation due to infection. The cytokines TNF-α and IL-6 are important in creating lethal sepsis, and by down-regulating their production, endotoxin shock can be avoided. This is shown in EXAMPLE 1.

The present invention provides for a method of treating inflammation in a subject, by administering a composition including hydrogen, releasing hydrogen in the body of the subject, down-regulating inflammatory responses of monocyte lineage cells, and measuring the down-regulation. The down-regulation of inflammatory responses can include down-regulation of TNF-α, IL-6, and IL-12p40, which are proinflammatory cytokines. The down-regulation of each of these cytokines can be measured to confirm that inflammation is being treated by the composition of the present invention. The monocyte lineage cells can be bone marrow derived macrophages (BMMs) and dendritic cells (DCs). Preferably, the composition including hydrogen is the NIW. This method is further described in EXAMPLE 2.

The present invention provides a method of suppressing hydroxyl radical in a subject, by administering a composition including hydrogen, releasing hydrogen in the body of the subject, suppressing hydroxyl radical, and measuring the amount of hydroxyl radical in the subject. By measuring the amount of the hydroxyl radical after administration of the composition, it can be confirmed that the hydroxyl radical has been suppressed. Preferably, the composition including hydrogen is the NIW, but the composition can also be any of those described above. This method is described in greater detail in EXAMPLE 3 below. The presence of hydroxyl radical indicates that possible tissue damage is caused in the context of inflammatory responses as well as oxidative stress. Among three major ROSs (hydroxyl radical, hydrogen peroxide and superoxide anion), it has been demonstrates that hydroxyl radical is the most toxic ROS that causes tissue damage. Since previous studies demonstrated that H2 inhibits the ROS (especially hydroxyl radical)-mediated oxidative tissue injuries, it was thought that the biological action of H2 is solely related to its anti-oxidant effects. Therefore, while the potency of H2-enriched water to scavenge hydroxyl radical is shown in EXAMPLE 3, the results are confirmative to the past published studies.

The present invention provides for a method of treating inflammation, by administering a composition including hydrogen, releasing hydrogen in the body, suppressing mitogen-activated protein kinase (MAPK) phosphorylation, down-regulating inflammatory responses, and measuring the amount of MAPK phosphorylation to confirm inflammatory responses are down-regulated. Preferably, the composition including hydrogen is the NIW, but the composition can also be any of those described above. This method is described in EXAMPLE 4. Furthermore, the suppression of MAPK phosphorylation occurs independently of ROS scavenging. This is further described in EXAMPLE 5. The mechanism by which hydrogen suppresses MAPK phosphorylation is by the up-regulation of the expression of MKP-1 protein on BMMs and DC. This mechanism is described in EXAMPLES 7-9. The measuring step can also more specifically be performed by measuring the amount of MKP-1 protein in the body of the subject.

The present invention further provides for a method of reducing the basal level of phosphorylation of MAPKs in non-stimulated BMMs in a subject by administering a composition including hydrogen, releasing hydrogen in the body of the subject, and reducing basal levels of phosphorylation of MAPKs of extracellular signal-regulated kinase (ERK), p38, and c-Jun N-terminal kinase (JNK) in non-stimulated BMMs. Preferably, the composition including hydrogen is the NIW, but any other composition as described above can also be used. This is further described in EXAMPLE 6.

Each of these pathways described above can be adapted for use as a drug screen to test for various compounds that affect the various biomarkers described above. While each of these pathways can be tested alone with separate assays as described below, they can also be combined in a single assay.

For example, a drug screen to test for compounds that can treat endotoxin shock can include an assay for measuring the production of biomarkers IL-6 and TNF-α. Drug candidates can be applied to the assay, and if they are found to down-regulate IL-6 and TNF-α, the drug candidates can be identified as being successful in treating endotoxin shock.

A drug screen test to test for compounds that treat inflammation can include an assay for measuring the production of biomarkers TNF-α, IL-6, and IL-12p40 in monocyte lineage cells. Drug candidates can be applied to the assay, and if they are found to down-regulate TNF-α, IL-6, and IL-12p40, the drug candidates can be identified as being successful in treating inflammation.

A drug screen test to test for compounds that suppress the hydroxyl radical can include an assay for measuring the amount of the biomarker hydroxyl radical. Drug candidates can be applied to the assay, and if they are found to suppress hydroxyl radical, the drug candidates can be identified as being successful in treating hydroxyl radical.

The MAPK phosphorylation pathway can also be used as a drug screen to test for compounds that can act as anti-inflammatories. An assay can be created with BMMs and/or DC, and various anti-inflammatory drug candidates can be applied to this assay. If the biomarker MKP-1 is found to be up-regulated by a drug candidate, this indicates that a drug candidate can be used as an anti-inflammatory drug that will work on the MAPK phosphorylation pathway. If MKP-1 is not found to be up-regulated, then this drug candidate should not be used as an anti-inflammatory drug for this specific pathway.

An assay can also be used as a diagnostic device to diagnose patients with inflammation or other conditions resulting from the MAPK pathway as discussed above and prescribe appropriate treatment as a method of personalized medicine. As inflammation can be caused by many different factors or pathways, identification of the correct pathway is important for prescribing the right treatment. Therefore, an assay can include measurements of the biomarkers IL-6, TNF-α, IL-12p40, hydroxyl radical, MKP-1, or combinations thereof. A sample from a patient can be applied to the assay, and if up-regulation or down-regulation of the biomarkers is found as described above compared to a normal control value, the MAPK pathway can be indicated in causing the inflammation or other condition, and a composition can be prescribed to specifically act on the MAPK pathway, such as those described herein. The assay can also be used to eliminate a possibility of a cause of inflammation or disease if up-regulation or down-regulation of the markers as described is not found, and the patient can be directed to alternative treatments that would better remedy their inflammation or other conditions.

While it is well described that the MAPK pathway plays a key role in development of cancer, such as melanoma, as well as inflammation which making it an important therapeutic target, because of low specificity and toxic side effects, few drugs have been developed in the past that specifically target this pathway. The challenge remains to identify the optimal members of the signaling cascade to target and drugs that are bioavailable with negligible toxicity-related side effects. The cross-talk between MAPK and other pathways, such as PI3K, also makes it difficult to develop specific chemical inhibitor for MAPKs. Thus far, several chemical compounds have been tested in the clinical trials for cancers and inflammatory diseases. However, most of the chemical compounds have been dropped off during the clinical trial due to the toxic side effects. For the resolution of inflammation, nonsteroidal anti-inflammatory drugs, (NSAIDs) have been developed and used most frequently. Even the most advanced class of (NSAIDs), i.e. COX-2 selective inhibitors, such as, Celecoxib, showed adverse side effects on the cardiovascular system, including increased risks of myocardial infarction, exacerbation of stable congestive heart failure, and worsening high blood pressure. Currently, there seems to be no sufficiently efficient anti-inflammatory drug that has no side effects. Because it is well known that hydrogen is released from gut commensal bacteria, it is considered that such bacteria derived hydrogen is not toxic to host body. Therefore, the novelty of this invention is derived from the hydrogen's possible side-effects free property that can still suppress the MAPK pathway.

EXAMPLES 1-8 below are all related to the MAPK pathways. However, the MAPK pathways have been sub-classed into 1) up-regulation, i.e. phosphorylation of MAPKs (Blue lines in FIG. 10) and 2) down-regulation pathways, i.e. dephosphorylation of MAPKs (Red lines in FIG. 10). Then, the up-regulation pathway is divided into two categories, A) ROS-independent (TLR2- and TLR3-induced up-regulation [Left side Blue line path lines in FIG. 10]) and 2) ROS-dependent pathways (TLR4-induced up-regulation [Right side Blue line path lines in FIG. 10]).

The present invention discloses that H2 can suppress the expression of proinflammatory cytokine via suppression of MAPKs phosphorylation. The H2-mediated induction of MKP-1 (an enzyme that dephosphorylates MAPKs) plays a role in suppression of MAPKs phosphorylation. Since previous studies demonstrated that H2 inhibits the ROS (especially hydroxyl radical)-mediated oxidative tissue injuries, biological actions of H2 are solely related to its anti-oxidant effects. However, the present invention has disclosed for the first time that H2-mediated MAPKs suppression occur in an ROS-independent manner, because H2 can suppress both ROS-dependent and ROS-independent MAPKs activations. Indeed, such H2-mediated MAPK-down-regulation is caused by MKP-1, of which induction does not involve ROS.

EXAMPLES 1-4 show the effects of H2 to suppress LPS induced inflammatory responses as well as the down-regulation of MAPKs phosphorylation (ROS-dependent MAPKs activation pathway is suppressed). EXAMPLE 5 shows that H2 can suppress ROS-independent MAPKs activation. EXAMPLE 6 shows that H2 reduces the basal level of phosphorylation of MAPKs, which does minimally or not require ROS. EXAMPLES 7-9 show the role of H2-induced MKP-1 in the context of H2-mediated inhibition of pro-inflammatory cytokine production.

The composition of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the composition of the present invention can be administered in various ways. Preferably, the composition including hydrogen is in the form of a neutraceutical, such as a drink that can easily be administered to a patient. It should be noted that it can be administered as the composition and can be administered alone or as an active ingredient in combination with pharmaceutically acceptable carriers, diluents, adjuvants and vehicles. The composition can also be administered orally, subcutaneously or parenterally including intravenous, intraarterial, intramuscular, intraperitoneally, intratonsillar, and intranasal administration as well as intrathecal and infusion techniques. Implants of the compositions are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the composition of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

MATERIALS AND METHODS FOR EXAMPLES 1-10

Animals:

C57BL/6j mice (6 to 7-week-old males) were kept in a conventional room with a 12-hour light-dark cycle at constant temperature. The experimental procedures employed in this study were approved by the Forsyth IACUC.

Measurement of Molecular Hydrogen:

Molecular hydrogen (H2) present in PBS or culture medium was measured using a needle-type Hydrogen Sensor (Unisense A/S, Aarhus, Denmark) following the method published by Hayashida et al.

Generation of H2 Dissolved Solution:

High purity H2 gas (Airgas, Salem, N.H.) was ejected into PBS or culture medium until H2 concentration reached to saturation (780 mM, at 25° C.). Then, H2 at appropriate concentration was prepared by dilution. The saturated H2 in water showed pH 7.6 and very high redox potential (ORP level −511 mV).

LPS Injection and Mouse Model of Endotoxin Shock:

LPS from *E. coli* 0111:B4 strain (Sigma, St. Louis, Mo.) was injected intraperitoneally (i.p.) at a dose of 35 mg/kg body weight. Further, mice were received PBS (0.6 ml/mouse [i.p.]) or H2-enriched PBS (780 mM 0.6 ml/mouse [i.p.]), or N-acetyl-L-cysteine (NAC, Sigma)-dissolved PBS (150 mg/kg body weight 0.6 ml/mouse [i.p.]) both 15 minutes and 1 hour after LPS injection. The plasma was collected 4 hour after LPS injection to measure the amount of TNF-a and IL-6 by ELISA assay as described below. The mice were observed 5 days to determine their survival rate.

Generation and Culture of Bone Marrow Derived Macrophages (BMMs) or Dendritic Cells (DCs):

Bone marrow cells were flushed from tibiae and femurs from 7 week old male mice. Bone marrow derived macrophages (BMMs) were differentiated as previously described with minor modification. Briefly, the cells were seeded in 6-well culture plates at a density of $1.0\times10^6$ cells/ml in Minimum Essential Medium Alpha (a-MEM, Sigma) supplemented with, penicillin G solution (100 U/ml, GIBCO; Invitrogen, Buffalo, N.Y.), streptomycin (100 mg/ml, GIBCO; Invitrogen), and gentamicin (50 mg/ml, GIBCO; Invitrogen) (medium A) containing 10% FBS (Hyclone Laboratories, Logan, Utah) and recombinant mouse (rm) M-CSF (100 ng/ml, Peprotech, Rocky Hill, N.J.) at 37° C. in 5% CO2 and cultured for 5 days. On day 6 of the culture, differentiated BMMs were harvested for experiments. For differentiation into DCs, bone marrow cells were plated in 6-well culture plates at a density of $1.0\times10^6$ cells/ml in RPMI 1640 (GIBCO; Invitrogen) supplemented with 10% FBS, penicillin G solution (100 U/ml), streptomycin (100 mg/ml), and 50 mg/ml gentamicin and rm GM-CSF (20 ng/ml, Peprotech) at 37° C. in 5% CO2 for 6 days and differentiated DCs were harvested for analysis on day 7.

The BMMs or DCs were seeded at a density of $1.0\times10^6$ cells/ml in 24-well or 96-well culture plates and maintained for 24 hours. The cells were precultured in medium A containing 2% FBS (medium B) with presence or absence of H2 for 30 min utesor pretreated with or without NAC (1 mM) for 30 min in medium B. Then the cells were exposed to LPS (1 mg/ml, Invivogen, Invivogen, San Diego, Calif.), PGN from *Staphylococcus aureus* (10 mg/ml, Invivogen), or poly(I:C) (10 mg/ml, Invivogen) for specified periods before the end of incubation.

Measurement of Proinflamatory Cytokines by ELISA:

Proinflamatory cytokines contained in plasma or cell culture supernatant were analyzed for TNF-a, IL-6, and IL-12p40 by using ELISA kits (Peprotech) following the instructions provided by the manufacturer.

Measurement of ROS Productions:

Intracellular levels of ROS stimulated by LPS was measured by using fluorescent probes: 2-[6-(4'-hydroxy)phenoxy-3H-xanthen-3-9-yl]benzoate (HPF) (Cayman, Ann Arbor, Mich.) detects hydroxyl radical specific or 5-(and-6)-carboxy-2',7'-dichlorodihydrofluorescein diacetate, acetyl ester (CM-H2DCFDA) (Molecular Probes; Invitrogen) detects superoxide, H2O2, and hydroxyl radical. In brief, cells were preincubated in phenol red free hank's buffer solution containing 0.5% FBS with 5 mM HPF or 5 mM CM-H2DCFDA with or without H2 at 37° C. for 30 minutes. After preculture, the cells were exposed to LPS (1 mg/ml) for 30 minutes and immediately HPF fluorescence or fluorophore DCF were detected at an excitation wavelength of 485 nm and an emission wavelength of 530 nm with a fluorometric imaging plate reader, Synergy HT (Biotech Instruments, Winooski, Vt.).

Immunoblotting:

Cells were lysed in buffer containing 25 mM Tris-HCl (ph 7.4), 150 mM NaCl, 5 mM EDTA (ph 8.0), 0.1% SDS, 1% NP-40, 10% Glycerol, and 1% (v/v) Triton X-100 (lysis buffer). The lysates were sonicated for 8 seconds on ice and were subjected to SDS/PAGE (12% gel) electrophoresis and proteins were electrophoretically transferred onto nitrocellulose membrane (Bio-Rad Laboratories, Hercules, Calif.). The membranes were blocked with 5% skim milk for 1 hour and then reacted with rabbit anti-mouse phosphorylated ERK antibody (Cell signaling, Beverly, Mass.; 1:1000), rabbit anti-mouse total ERK antibody (Cell signaling, 1:1000), rabbit anti-mouse phosphorylated p38 antibody (Cell signaling, 1:1000), rabbit anti-mouse total p38 antibody (Cell signaling, 1:500), rabbit anti-mouse phosphorylated JNK antibody (Cell signaling, 1:500), rabbit anti-mouse total JNK antibody (Cell signaling, 1:500), and HRP conjugated mouse anti β-actin antibody (abcam, Cambridge, Mass.; 1:30,000) at 4° C. overnight. After the membrane was washed, it was incubated with HRP-conjugated Donkey anti-rabbit IgG antibody (Jackson lmmunoresearch, West Grove, Pa.; 1:5000) for 1 hour at room temperature. After further washing, immunodetection was performed by using Immobilon Western Chemiluminescent HRP substrate (Millipore, Billerica, Mass.).

Collection of Peritoneal Cells:

The 6-week-old male mice (n=6/group) were received i.p. 1 ml of PBS solution with or without 780 uM of H2 or 150 mg/kg body weight of NAC. After 45 minutes, peritoneal suspensions were obtained by peritoneal lavage as previously described. Briefly, 4 ml of cold PBS were injected intraperitoneally, then the abdomen was massaged and the peritoneal exudates cells were collected allowing recovery of 90% of the injected volume. The peritoneal cells were immediately lysed in lysis buffer and performed Immunoblotting as described above.

RNA Interference (RNAi) for MKP-1 and MAT2s:

In order to silence the MKP-1 mRNA, BMM cells were treated with siRNA in Transmessenger™ Transfection Reagent (Qiagen, Tokyo, Japan). Briefly, the BMM cells were gently washed with antibiotics- and FBS-free D-MEM three times. The cells were incubated with the mixture between transfection reagent (Lipofectamin LTX, Invitrogen) and siRNA for mouse MKP-1 or mouse MAT2a (Stealth RNAi, Invitrogen). In order to confirm the lack of off-target effects by siRNA, non-target siRNA was used as a control. The efficiency of target mRNA suppression was monitored by RT-PCR specific to mouse MKP-1 or and MAT2a. The RNAi-mediated suppressions of MKP-1 or MAT2a protein were also confirmed by western blot analysis.

Immunofluorescent Staining of MKP-1 and HLA-DR:

Human gingival tissue isolated from periodontally healthy subject was fixed with a mixture of acetone (50%) and methanol (50%). Macrophages present in the colon were stained with anti-MKP-1-antibody (rabbit IgG, Santa Cruz) followed by FITC-conjugated anti-rabbit IgG and anti-HLA-DR (mouse IgG2a MAb) followed by TexasRed-anti-mouse IgG. The staining pattern was analyzed at 400 magnification using a Leica TCS/SP-2 laser scan con focal microscope.

Example 1

Figure 2:
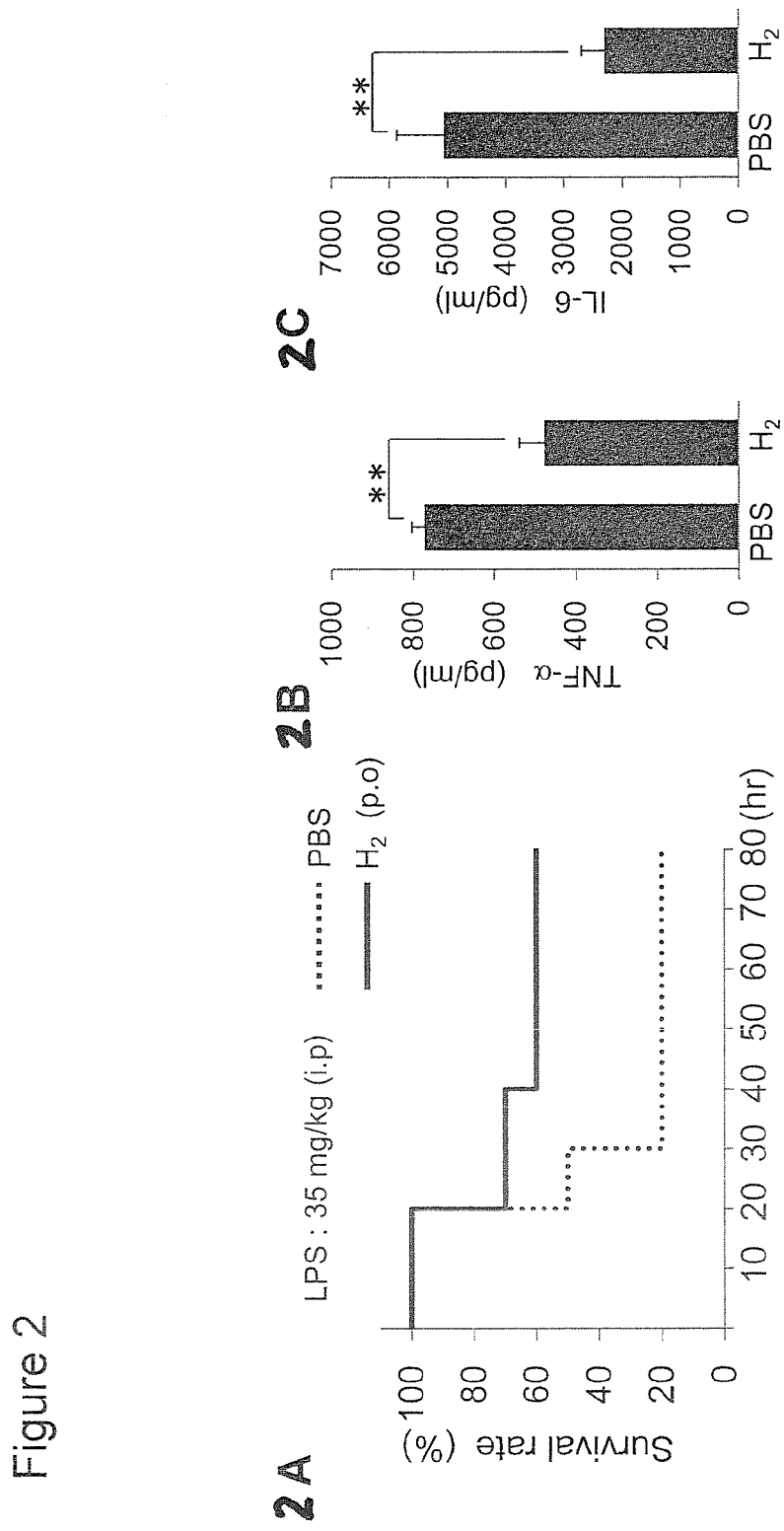
FIG. 2A is a graph of LPS challenge.
FIGS. 2B and 2C are graphs of production of TNF-α and IL-6, respectively.

Systemic Administration of H2 Dissolved Water Protects Mice from Lethal Endotoxin Shock Concomitant with the Suppression of Serum Proinflammatory Cytokines To investigate the effect of H2 on inflammation, the efficacy of systemic administration of H2 dissolved water (inter peritoneal: i.p.) was tested on LPS-induced endotoxin shock induced in C57BL/6j mice. The group of mice that received control PBS without H2 showed the survival rate of 40% at 30 hours after systemic injection of LPS (35 mg/kg, i.p.) and only 10% of the mice survived at the end of monitoring period (80 hours). However, the survival rate was increased to 90% by systemic injection of H2 (i.p.) at 80 hours after LPS challenge (FIG. 1A). As a control anti-inflammatory reagent, NAC, one of the most commonly used ROS inhibitors, was administrated to the mice received LPS injection. The survival rate of mice treated with NAC was 70% at 30 hours after LPS injection, and the final survival rate monitored at 80 hours was 20% (FIG. 1B), demonstrating similar potency to H2 in protecting mice from lethal endotoxin shock. Since elevated level of proinflammatory mediators, such as TNF-α and IL-6, play pivotal pathogenic roles in the LPS induced sepsis, the effects of NAC as well as H2 on serum concentrations of TNF-α and IL-6 in the mice received lethal dose of LPS. Both NAC and H2 significantly suppressed the production of TNF-α (FIG. 1C) and IL-6 (FIG. 1D) induced by lethal dose of LPS injection. It is noteworthy that, instead of systemic i.p. injection, oral administration of H2 dissolved PBS also prevented the mice from lethal endotoxin shock (FIG. 2A) along with the down-regulation of TNF-a and IL-6 production in serum (FIGS. 2B, 2C). These in vivo results indicated that H2 has remarkable protective effect on lethal endotoxin shock as potent as NAC.

Example 2

Figure 3:
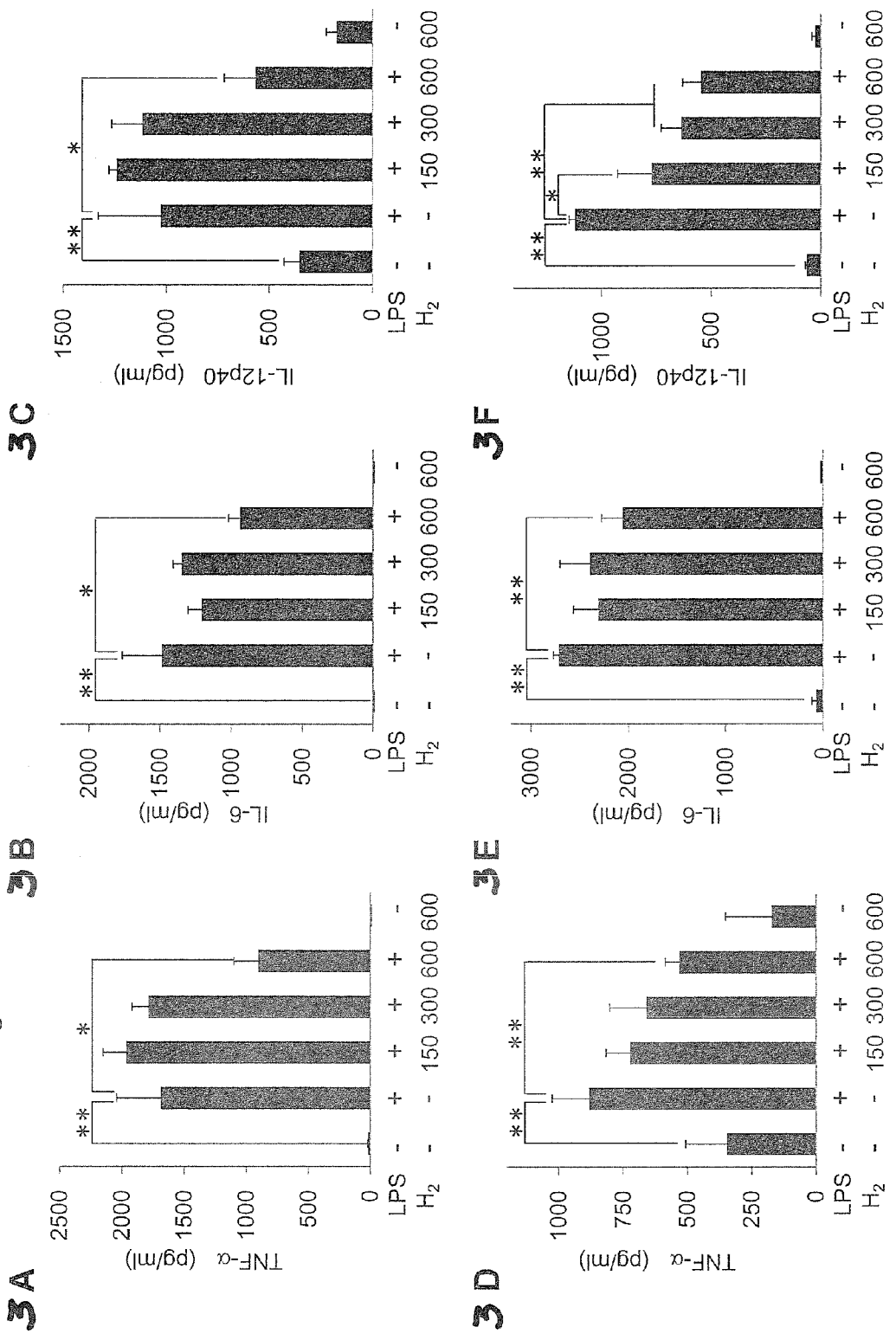
FIGS. 3A-3F are graphs of production of TNF-α, IL-6, and IL-12p40.

H2 Attenuates the LPS-Induced TNF-a and IL-6 Productions from Innate Immune Monocyte Linage Cells It is well documented that innate immune monocyte linage cells, such as macrophage or dendritic cells, are the prominent cellular sources of inflammatory cytokines in the context of endotoxic shock. Since H2 down-regulated the TNF-α and IL-6 production in the mice induced of lethal endotoxin shock (FIGS. 1 and 2), it is plausible that H2 can act on innate immune monocyte lineage cells to suppress their production of LPS-induced proinflammatory cytokines such as, TNF-α and IL-6. H2 dissolved in culture medium suppressed the TNF-α and IL-6 production from both BMMs (FIGS. 3A, 3B) and DCs (FIGS. 3D, 3E) in response to LPS stimulation. In addition, H2 also suppressed the IL-12p40 production inform LPS-stimulated BMMs as well as DCs (FIGS. 3C, 3F). These in vitro results demonstrated that H2 can suppress inflammatory responses by acing on innate immune monocyte lineage cells. Therefore, down-regulation of inflammatory responses by monocyte lineage cells may account for the H2-mediated suppression of LPS-induced lethal endotoxin shock in mice.

Example 3

H2 Selectively Reduces Hydroxyl Radical Induced by LPS-Stimulated Macrophages

Figure 4:
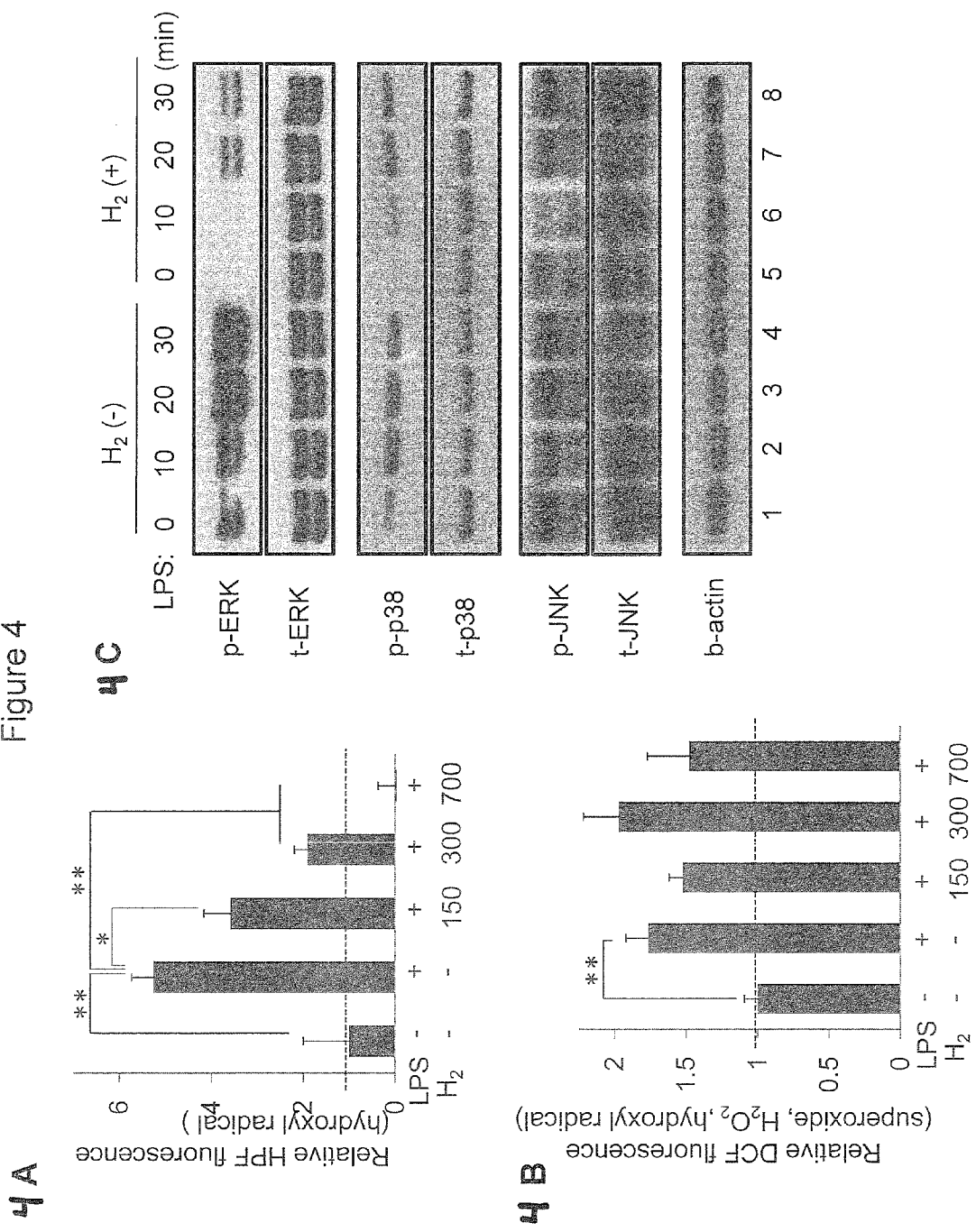
FIGS. 4A and 4B are graphs of relative fluorescence.
FIG. 4C is an immunoblot.

The effect of H2 on ROS production in BMMs stimulated by LPS was monitored. Both H2 and NAC suppressed the LPS-mediated induction of hydroxyl radical as monitored by the increased level of HPF (FIG. 4A). On the other hand, LPS-mediated induction of fluorescence from DCF which react to either superoxide, H2O2, or hydroxyl radical, was not affected by any concentrations of H2 tested (FIG. 4B), whereas NAC remarkably inhibited the fluorescence conversion from DCF. These results indicated that H2 can only suppress the most robust ROS, i.e. hydroxyl radical, while NAC suppress all three major ROS, i.e. superoxide, H2O2, and hydroxyl radical.

Example 4

H2 Suppresses the MAPKs Phosphorylation Induced by LPS-Stimulation

Mitogen-activated protein kinase (MAPK) signal transduction pathways play a key role in the inflammatory cell signaling, and inhibition of phosphorylation processes of MAPKs can down-regulate the inflammatory responses in the whole cell system. To examine the effects of H2 on MAPKs phosphorylation, BMMs were exposed to LPS in the presence or absence of H2, and increased phosphorylation of all three MAPKs (ERK, p38, and JNK) were detected by immunoblotting within 30 minutes after LPS-stimulation (FIG. 4C, lane 1-4). On the other hand, H2 obviously decreased phosphorylation level of MAPKs induced by stimulation with LPS (FIG. 4C, lane 5-8).

Example 5

Figure 5:
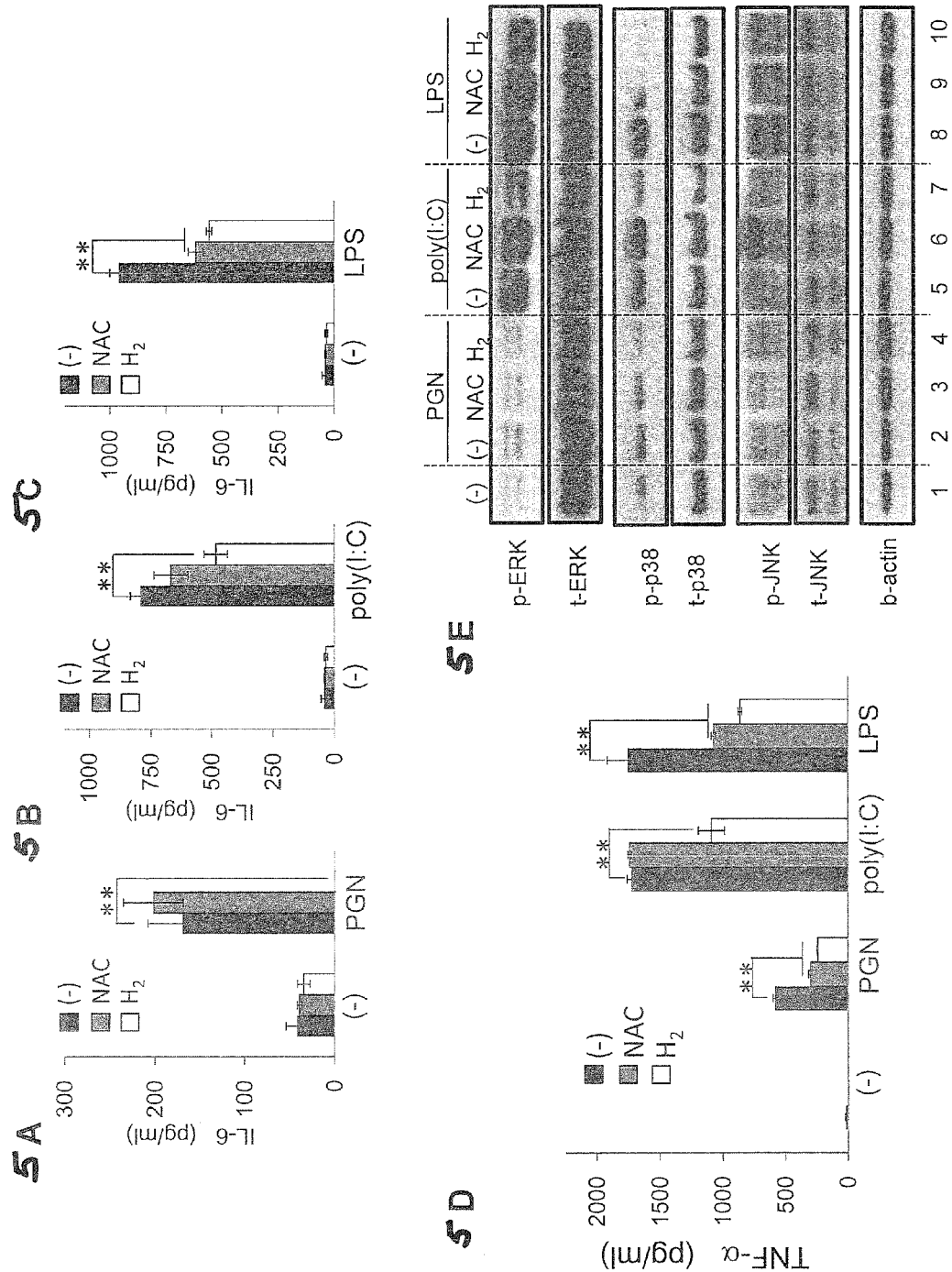
FIGS. 5A-5C are graphs of IL-6 production.
FIG. 5D is a graph of TNF-α production.
FIG. 5E is an immunoblot.

H2 Blocks ROS-Independent Signaling Cascade which Cause the Inflammatory Response in BMMs The effects of H2 on proinflammatory cytokine productions and the levels of MAPKs phosphorylation in BMMs stimulated by PGN or poly(I:C) were explored. It is well described that ROS generation is not required for PGN-induced or poly(I:C)-induced phosphorylation of MAPKs. Interestingly, H2 down-regulated the IL-6 production induced by PGN or poly(I:C) as well as LPS stimulation (FIGS. 5A, 5B and 5C). In contrast to H2, the ROS inhibitor NAC did not inhibit the IL-6 expression induced by PGN or poly(I:C (FIGS. 5A and 5B), while NAC still inhibited the IL-6 expression induced by LPS (FIG. 5C). In addition, TNF-α production induced by poly(I:C) stimulation was suppressed by H2 treatment, but not by NAC (FIG. 5D).

Moreover, immunobloting assay showed that H2 blocked the PGN-induced phosphorylation of ERK and p38, whereas NAC inhibited little or no phospholyration of ERK and p38 induced by PGN-stimulation (FIG. 5E, lane 2-4). Similar to this result, poly(I:C)-induced MAPKs phosphorylation was also attenuated by H2 treatment but not NAC (FIG. 5E, lane 5-7). H2 and NAC showed similar suppressive effect on LPS-induced phosphorylation of p38 and JNK but the level of phosphorylated ERK was decreased only by H2 (FIG. 5E, lane 8-10).

In sum, these data shown in FIGS. 5A-E demonstrated that H2 can inhibit the inflammatory response by the suppression of MAPKs phosphorylation independent of the ROS scavenging mechanism. Since all past publications described biological effects mediated by H2 as being solely derived from H2's ROS scavenge effects, the finding of ROS-independent anti-inflammatory effects mediated by H2 is completely novel.

Example 6

Figure 6:
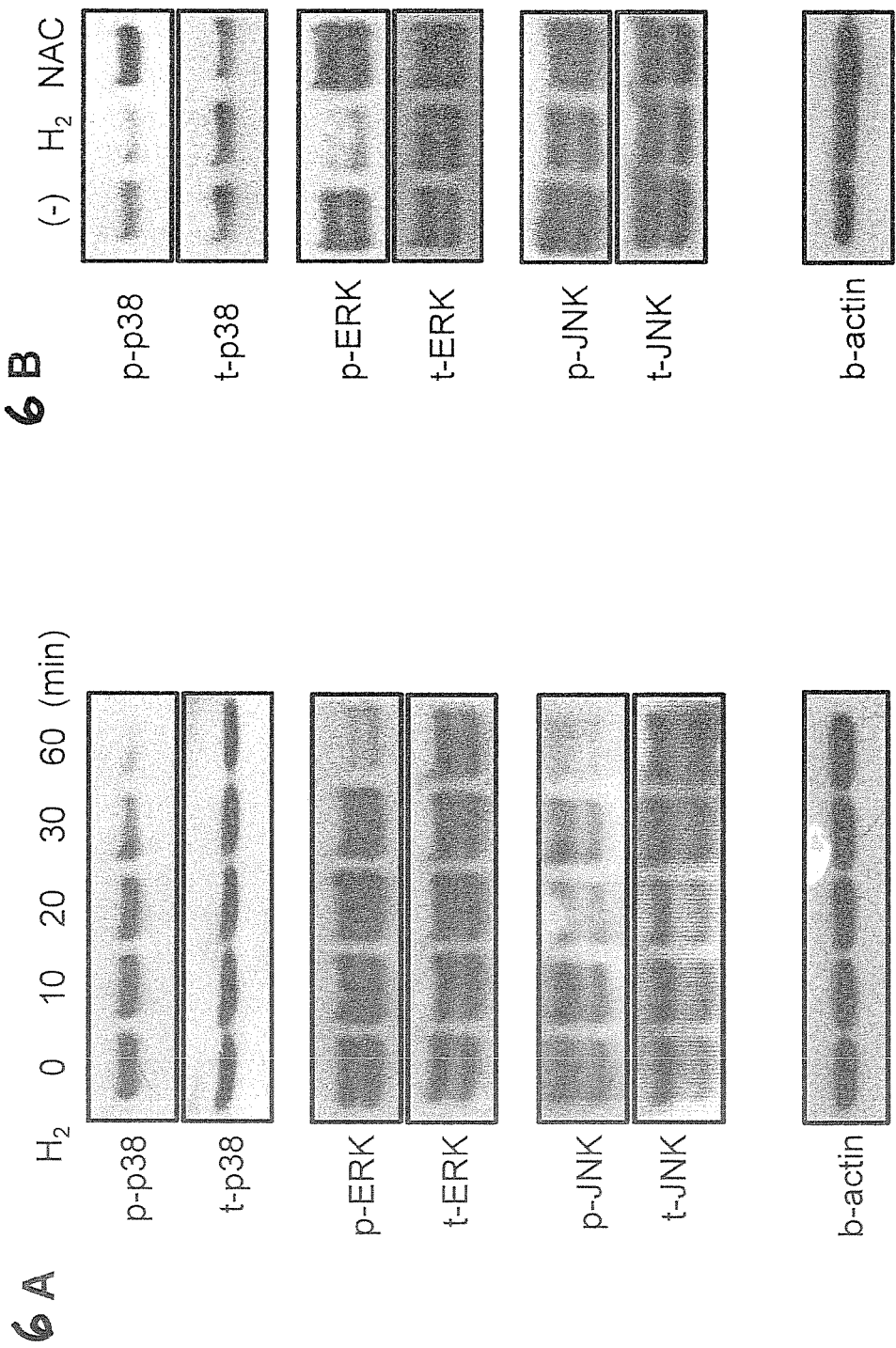
FIGS. 6A-6B are immunoblots.

H2 Reduces the Basal Level of Phosphorylation of MAPKs Sustained in Non-Stimulated Cells Since MAPK-signaling is engaged not only in inflammatory responses but also in cell growth and metabolism, basal level of MAPK-phosphorylation can be detected in most of cells. Based on in vitro assay, H2 treatment decreased the basal levels of phosphorylated ERK, p38, and JNK in non-stimulated BMMs in a time dependent manner (FIG. 6A). To confirm such effect of H2 to suppress basal level of MAPKs-phosphorylation in in vivo condition, phosphorylated MAPKs levels were examined in the peritoneal cells isolated from mice that received H2-PBS solution or NAC-PBS solution 45 minutes prior to the isolation. Although NAC did not reduce the levels of phosphorylation of MAPKs, H2 decreased the phosphorylation of all three MAPKs tested in peritoneal cells, majority of which are composed of macrophages (FIG. 6B). These findings suggested that H2 has biological effects to suppress phosphorylation of MAPKs induced by inflammatory stimuli as well as down-regulate the basal level of phosphorylation of MAPKs sustained in non-stimulated cells.

Example 7

H2 Up-Regulates the Production of MKP-1 Levels Directly In Vitro

Figure 7:
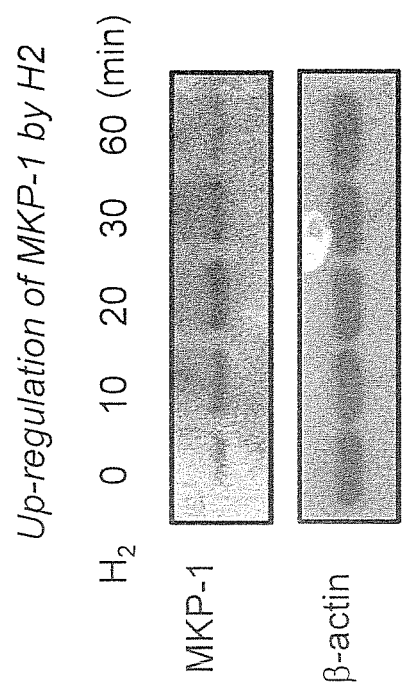
FIG. 7 is an immunoblot showing the up-regulation of MKP-1 by H2.

To elucidate the molecular mechanism underlying H2-mediated suppression of MAPKs phosphorylation, the involvement of MKP-1 was examined in the H2-stimulated BMMs, because MKP-1 can dephosphorylate all three members of the MAPK family. The exposure of H2 to BMMs up-regulated the expression of MKP-1 protein within 20 minutes, as shown in FIG. 7.

Example 8 siRNA-Mediated Inhibition of MKP-1 Protein Expression Results in the Abrogation of H2-Mediated Anti-Inflammatory Effects Among three MKP-1 specific siRNAs tested (#1, #2 and #3 in FIG. 8A), #1 siRNA sequence demonstrated most efficient suppression of MKP-1 protein production from BMMs. Using this anti-MKP-1 siRNA, compared to the negative control non-target siRNA, the suppression effects of H2 on the LPS induced IL-6 and TNF-α were examined in BMMs (FIGS. 8B and 8C). Although control non-target siRNA did not affect the H2-mediated suppression of IL-6 and TNF-α productions, anti-MKP-1 siRNA abrogated such H2-mediated effects to suppress LPS-induced productions of IL-6 and TNF-α. These data indicated that up-regulated expression of MKP-1 by H2 is responsible for the suppression of MAPKs-phosphorylation in LPS-stimulated BMMs.

Example 9

MKP-1 Expression in Monocyte-Linage Cells in Human Tissue

Figure 9:
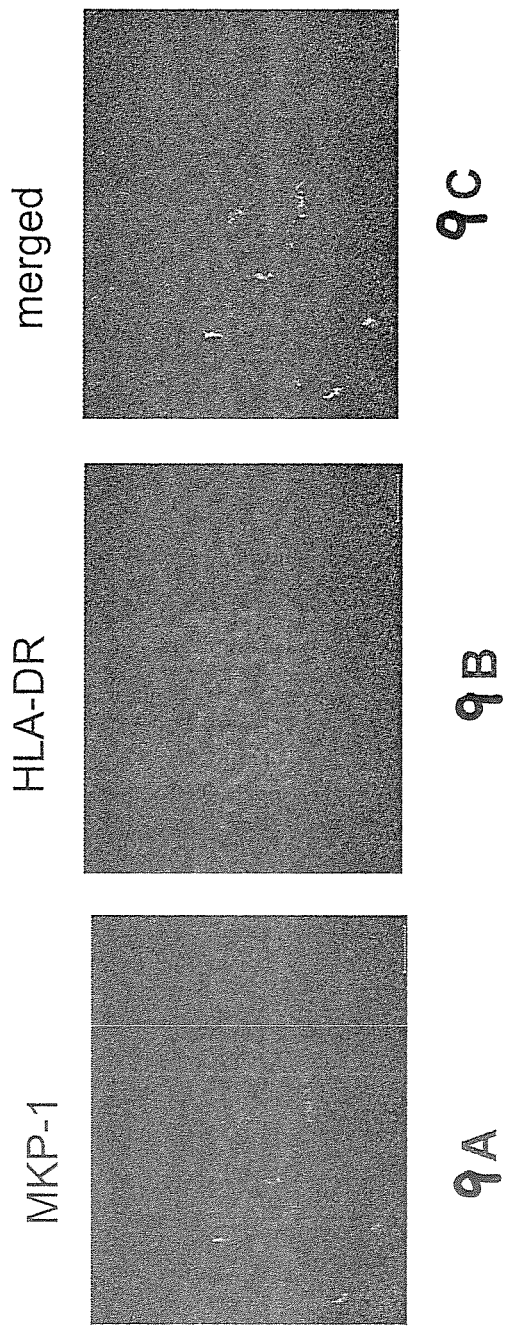
FIGS. 9A-9C are photographs of fluorescent immuno-histochemical staining of human gingival tissue.

Fluorescent immuno-histochemical staining demonstrated that, in human gingival tissue isolated from periodontally healthy subject, MKP-1 positive cells were found in HLA-DR expressing cells (FIGS. 9A-9C). Since HLA-DR is expressed on monocyte lineage cells, including macrophages and dendritic cells, macrophages and dendritic cells seem to be the major cells that express MKP-1. Based on the results shown above that the H2-mediated anti-inflammatory effects appeared to target macrophages (BMMs) and dendritic cells (DC), the evidence that MKP-1 is, indeed, expressed on macrophages and dendritic cells support the finding that increased MKP-1 in these monocyte lineage cells plays a key role in the H2-mediated suppression of MAPKs-phosphorylation and diminished expression of anti-inflammatory cytokines.

Example 10

Figure 10:
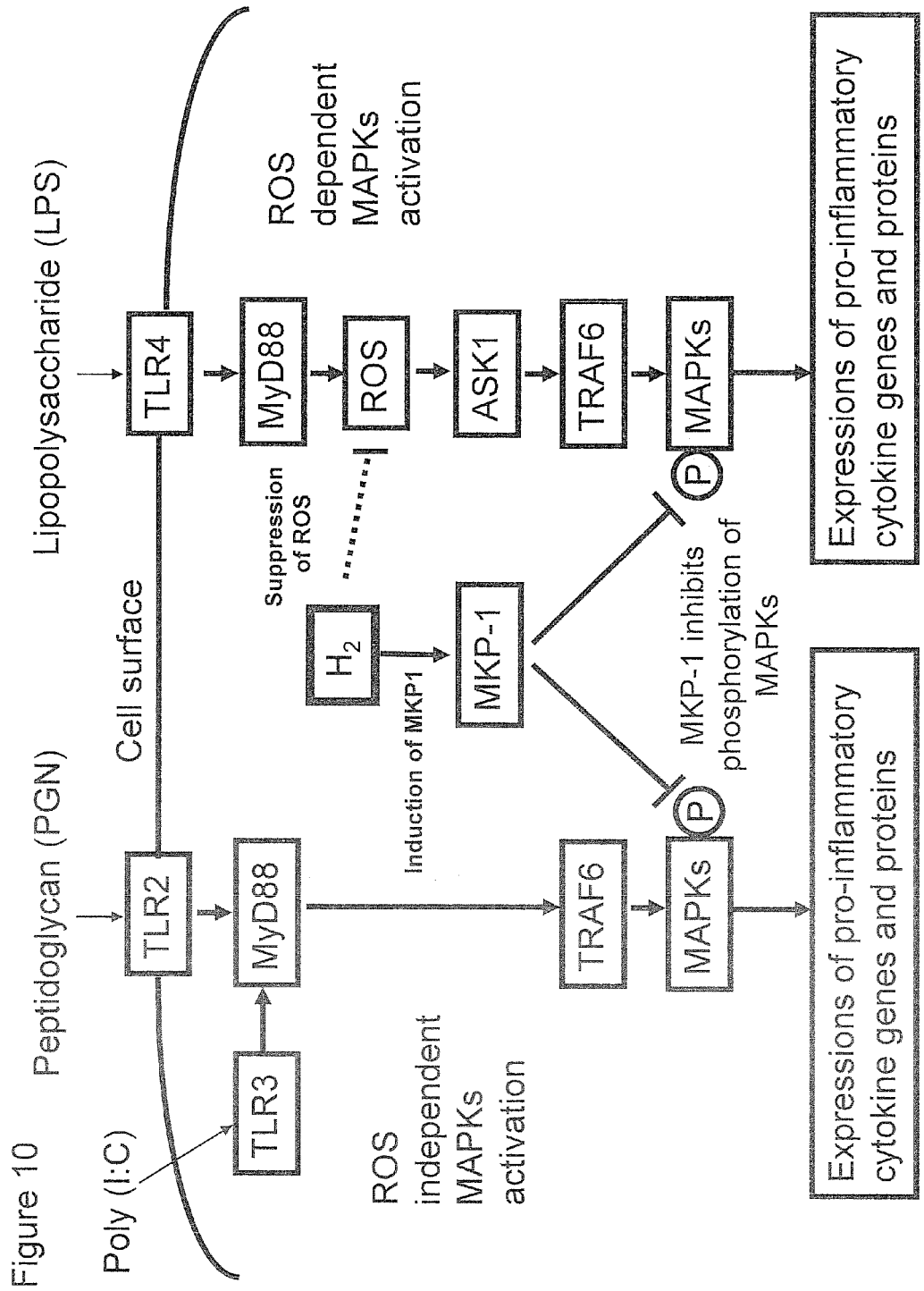
FIG. 10 is a schematic diagram showing the molecular cascade where H2 elicits the suppression of MAPK phosphorylation, which, in turn, down-regulates the production of pro-inflammatory factors.

First, MAPK pathways are divided into 1) up-regulation, i.e. phosphorylation of MAPKs (Blue lines in FIG. 10) and 2) down-regulation pathways, i.e. dephosphorylation of MAPKs (Red lines in FIG. 10). Then, up-regulation pathway is divided into two categories, A) ROS-independent (TLR2- and TLR3-induced up-regulation [Left side Blue line path lines in FIG. 10]) and 2) ROS-dependent pathways (TLR4-induced up-regulation [Right side Blue line path lines in FIG. 10]).

The present invention shows that H2 can suppress the expression of proinflammatory cytokine via suppression of MAPKs phosphorylation. The H2-mediated induction of MKP-1 (an enzyme that dephosphorylates MAPKs) appears to play a role in suppression of MAPKs phosphorylation. Since previous studies demonstrated that H2 inhibits the ROS (especially hydroxyl radical)-mediated oxidative tissue injuries, biological actions of H2 is solely related to its anti-oxidant effects. However, the present invention shows for the first time that H2-mediated MAPKs suppression occur ROS-independent manner, because H2 can suppress both ROS-dependent and ROS-independent MAPKs activations. Indeed, such H2-mediated MAPK-down-regulation is caused by MKP-1, of which induction does not involve ROS.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of treating inflammation in a subject, including the steps of:
    administering a composition to a subject which releases hydrogen gas in an amount effective to suppress mitogen-activated protein kinase (MAPK) phosphorylation and upregulate expression of MKP-1; and
    down-regulate inflammatory responses of monocyte lineage cells.

2. The method of claim 1, wherein said down-regulating step is further defined as down-regulating TNF-α, IL-6, and IL-12p40.

3. The method of claim 1, further including the step of measuring the down-regulation of TNF-α, IL-6, and IL-12p40 and confirming that inflammation is treated.

4. The method of claim 1, wherein the monocyte lineage cells are chosen from the group consisting of bone marrow derived macrophages (BMMs) and dendritic cells (DCs).

5. The method of claim 1, wherein the composition is neutral ionized water.

6. The method of claim 1, wherein the neutral ionized water is in a dosage form selected from the group consisting of a drink, a topical solution, and an injection.

7. The method of claim 5, wherein the neutral ionized water is a neutraceutical.

8. The method of claim 1, wherein the composition is chosen from the group consisting of water that is directly dissolved with hydrogen gas, a bacterium producing hydrogen, metal releasing hydrogen, and alloys releasing hydrogen.

9. The method of claim 1 wherein said administering further includes increasing the concentration of hydrogen gas in the subject.

* * * * *